United States Patent [19]

Dennis

[11] 4,180,680

[45] Dec. 25, 1979

[54] PREPARATION OF HALOPHENYLVINYLBENZYL ETHERS

[75] Inventor: Kent S. Dennis, Midland, Mich.

[73] Assignee: The Dow Chemical Company, Midland, Mich.

[21] Appl. No.: 928,663

[22] Filed: Jul. 28, 1978

[51] Int. Cl.$^2$ ............................................. C07C 41/04
[52] U.S. Cl. .................................................. 568/647
[58] Field of Search ..................... 260/612 R; 568/647

[56] References Cited

U.S. PATENT DOCUMENTS

| | | | |
|---|---|---|---|
| 2,121,723 | 6/1938 | Bass et al. | 260/612 R |
| 2,121,724 | 6/1938 | Bass et al. | 260/612 R |
| 2,392,733 | 1/1946 | Goddin et al. | 260/612 R X |
| 3,058,953 | 10/1962 | McMaster | 260/612 R X |

OTHER PUBLICATIONS

Krauch et al., Organic Name Reactions (1964) p. 491.

*Primary Examiner*—Bernard Helfin
*Attorney, Agent, or Firm*—Michael L. Glenn

[57] ABSTRACT

The title compounds are prepared in a process comprising contacting an alkali metal or alkaline earth metal salt of a tetra- or pentahalophenol with a vinylbenzyl chloride in a liquid, aqueous solvent containing from about 68 to about 90 weight percent of a $C_1$ or $C_2$ alkanol in a remaining amount of water. The contact of the aforementioned reactants occurs at a pH from about 7 to about 11 and at a temperature less than about 65° C. As an example, sodium pentachlorophenoxide can be reacted with vinylbenzyl chloride by this process in an aqueous methanol solvent (with about 20 weight percent water) to yield about 90 percent pentachlorophenylvinylbenzyl ether, based on vinylbenzyl chloride.

7 Claims, No Drawings

PREPARATION OF HALOPHENYLVINYLBENZYL ETHERS

BACKGROUND OF THE INVENTION

This invention relates to the preparation of a tetra- or pentahalophenylvinylbenzyl ether from the reaction of the corresponding halophenoxide with a vinylbenzyl chloride in an organic solvent.

U.S. Pat. No. 3,058,953 discloses that halo-phenylvinylbenzyl ethers can be prepared by the reaction of a halophenol with a vinylbenzyl chloride in the presence of aqueous alkali or alkaline earth hydroxide and a polymerization inhibitor in a liquid solvent. The solvent must be a highly polar one such as dioxane or dimethylformamide in admixture with water. This method of preparing a halophenylvinylbenzyl ether suffers from numerous deficiencies which have limited its utility. First, this method utilizes high boiling solvents, such as dioxane and dimethylformamide, which are difficult to remove from the precipitated product of the reaction. Second, the presence of excess hydroxide ions can hydrolyze vinylbenzyl chloride to vinylbenzyl alcohol. The vinylbenzyl alcohol in turn reacts with vinylbenzyl chloride to produce vinylbenzyl ether, an undesirable cross-linking compound in any subsequent vinyl polymerization of the product.

In view of the aforementioned deficiencies in the prior art method, it would be highly desirable to provide a method of preparing halophenylvinylbenzyl ether free of such contaminants.

SUMMARY OF THE INVENTION

A process has now been discovered for the preparation of a vinylbenzylhalophenyl ether having the formula:

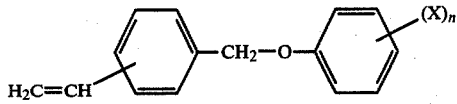

wherein X is chlorine or bromine and n is an integer 4 or 5. The process comprises reacting by contacting an alkali metal, alkaline earth metal or ammonium ion salt of a halophenol with a vinylbenzyl chloride in a liquid reaction medium consisting essentially of an aqueous solution of from about 68 to about 90 weight percent of at least one $C_1$ or $C_2$ alkanol with a remaining amount of water. The pH of the reaction medium is from about 7 to about 11 and the reaction temperature is less than about 65° C.

DETAILED DESCRIPTION OF THE EMBODIMENTS

The organic solvent can be a mixture of methanol, ethanol or both alkanols with water, but methanol-water mixtures are preferred. Sufficient water must be present in the solvent to solubilize the phenol salt. However, where the water in the solvent exceeds about 32 percent by weight, the halophenylvinylbenzyl ether cross-links upon polymerization to an unacceptable degree. Advantageously, water constitutes about 10 to about 25 weight percent of the solvent.

The alkali metal, alkaline earth metal or ammonium ion salt of a halophenol utilized as a reactant can bear 4 or 5, preferably 5, bromine or chlorine substituents. Advantageously, the halophenol salt is a sodium or potassium halophenoxide. The halophenol salt can conveniently be introduced by first adding a halophenol compound to the organic solvent. A suitable hydroxide, such as sodium or potassium hydroxide, is then added to the solvent until the halophenol is neutralized to the halophenoxide; in this neutralization, care should be taken to avoid the addition of any excess hydroxide. The halophenol is generally substantially completely neutralized at a pH greater than about 7. However, a pH of from about 7 to about 10 is preferred, more preferably about 7.5 to about 9.6. This endpoint can be determined by the use of a suitable indicator, such as thymol blue.

It is advantageous to add the vinylbenzyl chloride slowly to a solution containing a stoichiometric excess of the preformed halophenoxide. Excess halophenoxide encourages rapid reaction and minimizes undesirable reactions, such as that between vinylbenzyl chloride and its hydrolysis product. Desirably, during the reaction the halophenoxide is at all times present in a stoichiometric ratio relative to the vinylbenzyl chloride greater than about 1:1, preferably greater than about 1.1:1.

The reactants are desirably brought together in the mixture of alkanol and water at a temperature of from about 25° C. to about 65° C., preferably about 50° C. to about 60° C. Lower and higher temperatures than the aforementioned ranges are operable, but lower temperatures generally result in uneconomically slow rates of reactions and higher temperatures can produce undesirable polymerization in a reaction medium free of polymerization inhibitors. Polymerization inhibitors can be present in small amounts in the reaction medium, but are not generally necessary.

The halophenylvinylbenzyl ether product precipitates from the reaction medium to form a slurry. The crude product can be separated from the medium in any manner known in the art. Conveniently, this product slurry can be collected and filtered, the filtrate being recycled to the reaction medium. The crude product is washed with a very dilute aqueous solution of a hydroxide or other base which renders the wash barely basic. The product is then washed with water to remove salts of chloride and occluded phenol salts. The water-washed product is then washed with an organic solvent in which the product is not soluble to remove traces of vinylbenzyl chloride and like impurities. The washed product is dried at a temperature less than about 50° C., preferably less than 25° C., to avoid polymerization.

The examples that follow further illustrate the invention, but are not to be taken as limiting its scope.

EXAMPLE 1

A solution of 1200 grams (4.5 moles) of pentachlorophenol with 36 drops of a 1 weight percent solution of thymol blue in pyridine is introduced into 2700 grams of methanol. The methanol solution is then titrated with a 25.9 weight percent aqueous solution of potassium hydroxide until the blue endpoint of the thymol blue indicator is reached.

The methanol-water solution (75 percent methanol in solvent by weight) containing the potassium pentachlorophenoxide is then introduced into a two-gallon glass lined reactor, and is purged with and maintained under a nitrogen atmosphere. A mass of 325.2 grams (2.13 moles) of mixed isomers of vinylbenzyl chloride is added dropwise with stirring to the potassium pentachlorophenoxide solution at a temperature of 55° C. over a period of 130 minutes. The reaction medium is stirred after the addition of vinylbenzyl chloride for about 15 hours. The product and potassium chloride is observed to precipitate as a slurry.

After stirring for 15 hours, a small portion of the slurry is periodically removed from the reactor, diluted with water and acidified with $HNO_3$ to a pH of about 6. The acidified slurry is centrifuged and the liquid is separated from the solids in the slurry. These solids are once more diluted with water, centrifuged and the liquid separated. The two liquid portions are combined and analyzed by any standard method for chloride ions (from the potassium chloride by-product) to determine the extent of reaction. The stirring of the reaction medium is continued until the chloride analysis indicates substantially complete reaction.

The reactor is then drained, the solids filtered from the reaction medium and the supernatant liquid saved. The solids are washed with 3000 milliliters (ml) of a very dilute aqueous solution of potassium hydroxide. The solids are once more filtered and washed with 3000 ml of water followed by a wash with an equal volume of methanol at 20° C. The solids are filtered, washed with methanol at about 65° C. and immediately filtered once more. The product is dried at room temperature to small friable beads. The beads are ground once more, washed with water and dried at room temperature.

A 708 gram mass of product is recovered representing a yield of 86 weight percent, based on vinylbenzyl chloride. This product is a fine precipitate barely off-white in color which is identified as isomers of vinylbenzylpentachlorophenyl ether. The product is readily thermally polymerized to a polymer soluble in toluene, xylene, and the like.

EXAMPLE 2

The supernatant liquid from Example 1 is combined with 600 grams of pentachlorophenol, 1341 grams of methanol and 18 drops of a 1 percent by weight solution of thymol blue in pyridine to prepare a new reaction medium. The reaction medium is titrated with a 24.7 weight percent solution of aqueous potassium hydroxide in the manner of Example 1 and sufficient additional water is then added to the medium to increase the total water added to the supernatant liquid to 450 grams. The vinylbenzyl chloride is added dropwise to the reaction medium and the reaction is carried out in the manner of Example 1.

After chloride analysis indicates 80 percent of the vinylbenzyl chloride has reacted, the reactor is drained. The solids are collected and filtered and the supernatant liquid saved. The solids are bathed in washes of aqueous potassium hydroxide, water, cold methanol and hot methanol as described in Example 1. The solids are then dried at room temperature to a fine powder in appearance.

A 628 gram mass of vinylbenzylpentachlorophenyl ether is recovered representing a yield of 77 weight percent, based on vinylbenzyl chloride. This embodiment demonstrates that the supernatant liquid from the reaction medium can be recycled. Th recycling is limited by the accumulation of water in the reaction medium.

EXAMPLE 3

The supernatant liquid from Example 2 is used to prepare a new reaction medium and the reaction is carried out in the manner of Example 2. After chloride analysis indicates 90 weight percent of the vinylbenzyl chloride has reacted, the reactor is drained.

The solids are collected, filtered and bathed in washes of potassium hydroxide, water, cold methanol and hot methanol as described in Example 1. The solids are then dried at room temperature to a fine precipitate in appearance. A 585.5 gram mass of vinylbenzylpentachlorophenyl ether is recovered.

The reactor is opened and a large amount of solids collected from above the liquid line. These solids are washed and treated like any other crude product. A 199.6 gram mass of vinylbenzylpentachlorophenyl ether is recovered.

The total product mass recovered in Examples 1, 2 and 3 is 2121.1 grams. This represents an overall yield of 87 weight percent based on the vinylbenzyl chloride. This is a significant improvement in yield over the 56.5 percent reported in U.S. Pat. No. 3,058,953.

EXAMPLE 4

In a manner otherwise similar to the method set out in Example 1, the reaction between vinylbenzyl chloride and pentachlorophenoxide is carried out in a series of runs at a variety of weight percent concentration of water in the organic solvent and a variety of molalities of water in the total reaction medium. The collected and dried product is then thermally polymerized to poly(vinylbenzylpentachlorophenyl ether). The resulting polymer is introduced into tetrahydrofuran to determine whether sufficient cross-linking occurs during polymerization to render the polymer insoluble. The terms soluble and insoluble convey the same meaning to one skilled in the art as that set out in *Handbook of Chemistry and Physics*, p. C-62, CRC Press (1977). The molality of the water in the total solution, the stoichiometric ratio of pentachlorophenoxide (PCP) to vinylbenzyl chloride (VBC) as well as other operating parameters are tabulated in Table I for each run.

TABLE I

| Run No. | PCP:VBC | % $H_2O$ in Solvent | Molality $H_2O$ | Polymer Solubility |
|---|---|---|---|---|
| 1 | 2:1 | 20.0 | 7.71 | Soluble |
| 2 | 1.5:1 | 20.0 | 8.55 | Soluble |
| 3 | 3:1 | 28.5 | 9.05 | Soluble |
| 4 | 1.5:1 | 25.0 | 10.84 | Soluble |
| 5 | 2:1 | 31.4 | 11.79 | Soluble |
| 6 | 1.5:1 | 30.0 | 13.00 | Soluble |
| 7* | 3:1 | 33.0 | 9.55 | Insoluble |
| 8* | 3:1 | 38.0 | 11.70 | Insoluble |

*Not an embodiment of the invention.

The data in Table I indicates that the weight percent water in the methanol-water solvent is the critical factor in determining whether or not an undesirable amount of cross-linker forms rendering polymers of the product insoluble. Greater than 32 weight percent water produces the cross-linking agent as in Runs 7 and 8. The molality of the water in the total reaction medium can be increased to accelerate the reaction without producing cross-linking, so long as the stipulated weight percent water in the solvent excluding the reactants is not exceeded.

EXAMPLE 5

A solution of 22.4 grams of pentabromophenol dissolved in 66.7 grams of methanol containing 1 drop of a 1 weight percent solution of thymol blue in pyridine is titrated with a 4.7 weight percent aqueous solution of potassium hydroxide until the blue endpoint is reached.

The methanol-water solution of the potassium pentabromophenoxide is introduced into a glass reactor in a nitrogen atmosphere. Then 3.82 grams of mixed isomers of vinylbenzyl chloride is added dropwise to the reaction medium at a temperature of 65° C. over a period of 8 minutes. The medium is then stirred for one hour and a precipitate is observed. The extent of reaction monitored in the manner of Example 1 is found to be 98.8 percent.

The precipitate is collected and purified by washing as described in Example 1. A 12.5 gram mass of vinylbenzylpentabromophenyl ether is recovered after drying, which represents a yield of 89 weight percent based on vinylbenzyl chloride. The product is off-white in color and thermally polymerizes to a polymer soluble in o-dichlorobenzene.

EXAMPLE 6

A solution of 11.6 grams of 2,3,5,6-tetrachlorophenol dissolved in 44.2 grams of methanol containing 1 drop of a 1 weight percent solution of thymol blue in pyridine is titrated with a 23 weight percent aqueous solution of potassium hydroxide until the blue endpoint is reached.

The methanol-water solution of the potassium tetrachlorophenoxide is introduced into a glass reactor in a nitrogen atmosphere. Then 3.82 grams of mixed isomers of vinylbenzyl chloride is added dropwise to the reaction medium at a temperature of 65° C. over a period of 8 minutes. The reaction medium is stirred for a period of 3.5 hours. The extent of reaction monitored in the manner of Example 1 is found to be 71 weight percent after one hour and 89 weight percent two hours after the addition of the vinylbenzyl chloride.

The precipitate from the reaction is collected by filtration and purified with sequential washes with aqueous potassium hydroxide, water, cold methanol and hot methanol as described in Example 1. The product dissolves in the hot methanol, but most of the product crystallizes from the solution after cooling. A 6.3 mass of dried vinylbenzyl-2,3,5,6-tetrachlorophenyl ether is recovered, which represents a yield of 56 weight percent based on vinylbenzyl chloride. This yield is low because of the product lost in the methanol wash. The product thermally polymerizes with styrene at 50 weight percent solids in ethylbenzene to produce a soluble polymer.

COMPARATIVE EXAMPLE 7

In a manner otherwise similar to the method set out in Example 1, the reactor is pressurized slightly so that a higher reaction temperature can be effected. A solution of 106 grams of pentachlorophenol in 404 grams of methanol is reacted with an aqueous solution of sodium hydroxide to the blue endpoint of thymol blue. The liquid methanol-water solution (78.5 percent methanol in solvent by weight) containing the sodium pentachlorophenoxide is reacted with 57.25 grams of vinylbenzyl chloride added dropwise over a period of 90 minutes to the solution at a temperature of 72° C. After chloride analysis indicates substantially complete reaction, the reactor is drained.

The solids are collected, filtered and washed. These solids contain hard agglomerates as large as one-half inch in diameter as well as fine powder. Hence, the product is in a less desirable form and contains occluded impurities when it is prepared at temperatures above about 70° C.

COMPARATIVE EXAMPLE 8

In a manner otherwise similar to the method set out in Example 1, 197.5 grams of 2,4,5-trichlorophenol is reacted with an aqueous solution of potassium hydroxide in 520 grams of methanol to the blue endpoint of thymol blue. The methanol-water solution (77.5 percent methanol in solvent by weight) containing the potassium trichlorophenoxide is reacted with 76.33 grams of vinylbenzyl chloride added dropwise over a period of 200 minutes to the solution at a temperature of 60° C. After 48 hours of reaction, chloride analysis indicates about 82 percent of the vinylbenzyl chloride has reacted.

The reactor is drained and the product separates as a viscous liquid. The viscous liquid is dissolved in methylene chloride and washed with water. After evaporation of the methylene chloride, the liquid is introduced into a mixture of 75 weight percent acetone with 25 weight percent methanol and a precipitate is isolated. The precipitate gradually separates into solid needle-like crystals and a liquid. These crystals, when thermally polymerized, form a cross-linked polymer. The liquid polymerizes to a polymer soluble in o-dichlorobenzene. Hence, halophenoxides having less than 4 halogen substituents, when reacted in accordance with the claimed method, produce a less desirable product containing cross-linking compounds.

What is claimed is:

1. A process for the preparation of a vinylbenzylhalophenyl ether having the formula:

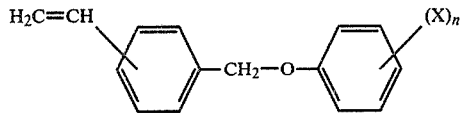

wherein X is chlorine or bromine and n is an integer 4 or 5, comprising the steps of:
(a) reacting by contacting an alkali metal, alkaline earth metal or ammonium ion salt of a halophenol, which corresponds to the formula:

wherein X and n have the aforesaid meanings, with a vinylbenzyl chloride in a liquid reaction medium consisting essentially of an aqueous solution of from about 68 to about 90 weight percent of at least one $C_1$ or $C_2$ alkanol with a remaining amount of water and wherein said contact occurs at a pH from about 7 to about 11 and a temperature less than about 65° C.; and
(b) separating the vinylbenzylhalophenyl ether from the liquid reaction medium.

2. The process as described in claim 1 wherein the alkanol is methanol.

3. The process as described in claims 1 or 2 wherein the aqueous solution contains from about 75 to about 90 weight percent of the alkanol.

4. The process as described in claim 2 wherein the reaction temperature is from about 25° C. to about 60° C.

5. The process as described in claim 2 wherein X is chlorine and n is the integer 5.

6. The process as described in claim 2 wherein X is bromine and n is the integer 5.

7. The process as described in claim 2 wherein n is the integer 5, the aqueous solution contains about 70 to about 76 weight percent methanol, and the contact occurs at a temperature of about 55° C. and a pH of from about 7.5 to about 9.6.

* * * * *